(12) United States Patent
Cao et al.

(10) Patent No.: US 9,795,718 B1
(45) Date of Patent: Oct. 24, 2017

(54) BIOCOMPATIBLE DEVICES WITH DISSOLVABLE SUBSTRATES AND METHODS OF FORMING THE SAME

(71) Applicant: International Business Machines Corporation, Armonk, NY (US)

(72) Inventors: Qing Cao, Yorktown Heights, NY (US); Ying He, Norwalk, CT (US); Ning Li, White Plains, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/229,497

(22) Filed: Aug. 5, 2016

(51) Int. Cl.
| | | |
|---|---|---|
| H01L 51/00 | (2006.01) |
| G01N 31/22 | (2006.01) |
| A61L 31/14 | (2006.01) |
| A61L 31/00 | (2006.01) |
| A61B 5/11 | (2006.01) |
| H01L 23/498 | (2006.01) |

(52) U.S. Cl.
CPC .......... *A61L 31/148* (2013.01); *A61B 5/1118* (2013.01); *A61L 31/00* (2013.01); *A61L 31/145* (2013.01); *H01L 23/49894* (2013.01)

(58) Field of Classification Search
CPC . A61L 31/10; H01L 21/28; H01L 2221/6834; H01L 51/0002
See application file for complete search history.

(56) References Cited

U.S. PATENT DOCUMENTS

| | | | |
|---|---|---|---|
| 5,427,096 A | | 6/1995 | Bogusiewicz et al. |
| 6,025,650 A | * | 2/2000 | Tsuji ..................... H01L 21/565 |
| | | | 257/668 |
| 7,217,426 B1 | | 5/2007 | Hossainy |
| 7,371,719 B2 | | 5/2008 | Stupp et al. |
| 8,666,471 B2 | | 3/2014 | Rogers et al. |
| 8,722,850 B2 | | 5/2014 | Vescovi et al. |
| 9,142,787 B2 | | 9/2015 | Omenetto et al. |
| 2006/0222565 A1 | * | 10/2006 | Hartig ..................... C07K 17/14 |
| | | | 422/400 |
| 2010/0108512 A1 | * | 5/2010 | Hattori ............. G01N 27/44791 |
| | | | 204/452 |
| 2013/0140649 A1 | | 6/2013 | Rogers et al. |
| 2016/0120472 A1 | * | 5/2016 | Kub ....................... A61B 5/686 |
| | | | 600/377 |

OTHER PUBLICATIONS

Bai S. et al., "Stable Emulsions Formed by Self-Assembly of Interfacial Networks of Dipeptide Derivatives", ACS Nano 8(7):7005-7013 (2014).
Dinca V. et at, "Directed Three-Dimensional Patterning of Self-Assembled Peptide Fibrils", Nano Letters 8 (2):538-543 (2008).
Kim D-H et al., "Silicon Electronics on Silk as a Path to Bioresorbable, Implantable Devices", Applied Physics Letters 95:133701-1-133701-3 (2009).

* cited by examiner

*Primary Examiner* — Jasmine Clark
(74) *Attorney, Agent, or Firm* — Scully, Scott, Murphy & Presser, P.C; Louis J. Percello, Esq.

(57) ABSTRACT

The present disclosure provides a method of forming a biocompatible structure that includes forming biodissolvable substrate comprising a flexible network of peptides, and a biocompatible structure having a biodissolvable substrate and, optionally, an electronic device on a surface thereof for use in implantable electronics.

18 Claims, 4 Drawing Sheets

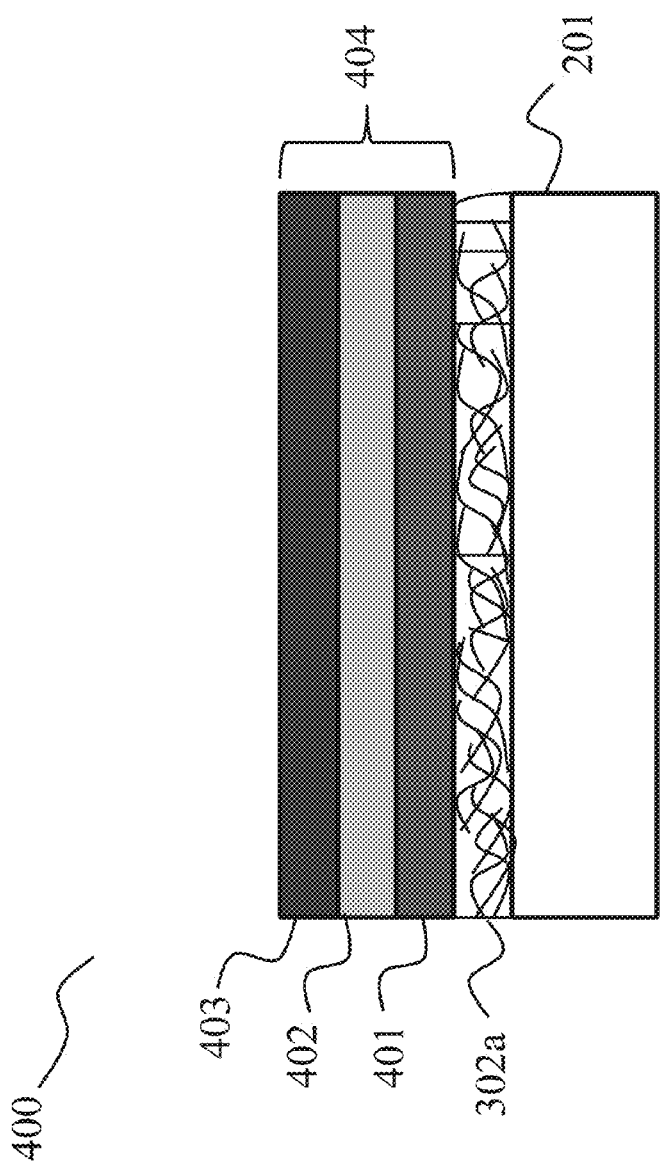

BIOCOMPATIBLE DEVICES WITH DISSOLVABLE SUBSTRATES AND METHODS OF FORMING THE SAME

BACKGROUND

The present disclosure relates to a biocompatible structure that includes a biodissolvable peptide-based hydrogel that forms a substrate as well as a method for forming the same.

Biocompatible electronic devices have important applications in today's society and have been used, for example, in monitoring of physiological disorders, cardiac intervention and pacing, and the treatment of muscular and central nervous system disorders. Prior art methods and devices incorporate flexible substrates made from silk. These substrates rely on the capability of silk to disintegrate in water, leaving behind only an amino-acid by-product that can be subsequently degraded by enzymes present in the human body. However, silk-based substrates either dissolve too slowly or incompletely, resulting in adverse biological side-effects, such as inflammation and irritation at the site of implantation. Thus, there is a need for providing biocompatible structures that have a combination of high sensitivity, flexibility and dissolve completely without harm to the subject.

SUMMARY

In one aspect of the present disclosure, a biocompatible structure is provided that includes a biodissolvable substrate composed of a flexible network of peptides. In certain embodiments, the biodissolvable peptides are a chain of at least two amino acids capable of self-assembly into fibers that form a flexible network of peptides. In other embodiments, the peptides that form the flexible network are peptide amphiphiles. In some embodiments, the biocompatible structure also includes an electronic device on the biodissolvable substrate. In specific embodiments, the electronic device includes at least one semiconductor component or electrode. In certain embodiments, the electronic device is formed directly on an exposed surface of the biodissolvable substrate. Optionally, the electronic device also includes one or more material layers, such as a gate stack formed on the substrate, whereby the gate stack comprises a gate dielectric, a gate electrode and, optionally, a gate dielectric cap. In some embodiments, the electronic device is supported by, and in physical contact with, the biodissolvable peptide-based substrate. In an embodiment, the biodissolvable substrate has a thickness of about 100 nanometers, about 200 nanometers or has a thickness of between 100 nanometers and 500 microns, inclusive. In specific embodiments, the biodissolvable substrate is tunable. In preferred embodiments, the biodissolvable substrate of the present disclosure completely decomposes on or within a subject without causing inflammation and/or irritation at the site of implantation.

In another aspect of the present disclosure, a method of forming a biocompatible structure is provided that, in one embodiment, includes providing a wafer, and depositing a solution of a plurality of peptides on the wafer to form a biodissolvable substrate (e.g., a hydrogel) on the wafer, which is comprised of a flexible network of peptides. In some embodiments, the method includes mixing a solvent, such as water, with a desired concentration of peptides (e.g., peptide amphiphiles) to form a peptide solution. This peptide solution can then be deposited on a surface of a wafer by, for example, spin coating to form a layer of peptide-based solution on the wafer. In certain embodiments, the method includes a heating step and subsequent cooling process that facilitates the formation of a peptide-based hydrogel on the surface of the wafer. In certain embodiments, an electronic device, such as a gate structure can then be formed on an exposed surface of the biodissolvable substrate and the substrate is then removed from the wafer. In other embodiments, the biodissolvable substrate is removed from the wafer leaving a flexible, biodissolvable, peptide-based substrate that can be, for example, implanted into a subject or affixed to the skin of a patient or animal.

BRIEF DESCRIPTION OF SEVERAL VIEWS OF THE DRAWINGS

FIG. 4 is a cross sectional view of an exemplary biocompatible structure having an electronic device on a topmost surface of the biodissolvable substrate of FIG. 3.

DETAILED DESCRIPTION

Figure 1:
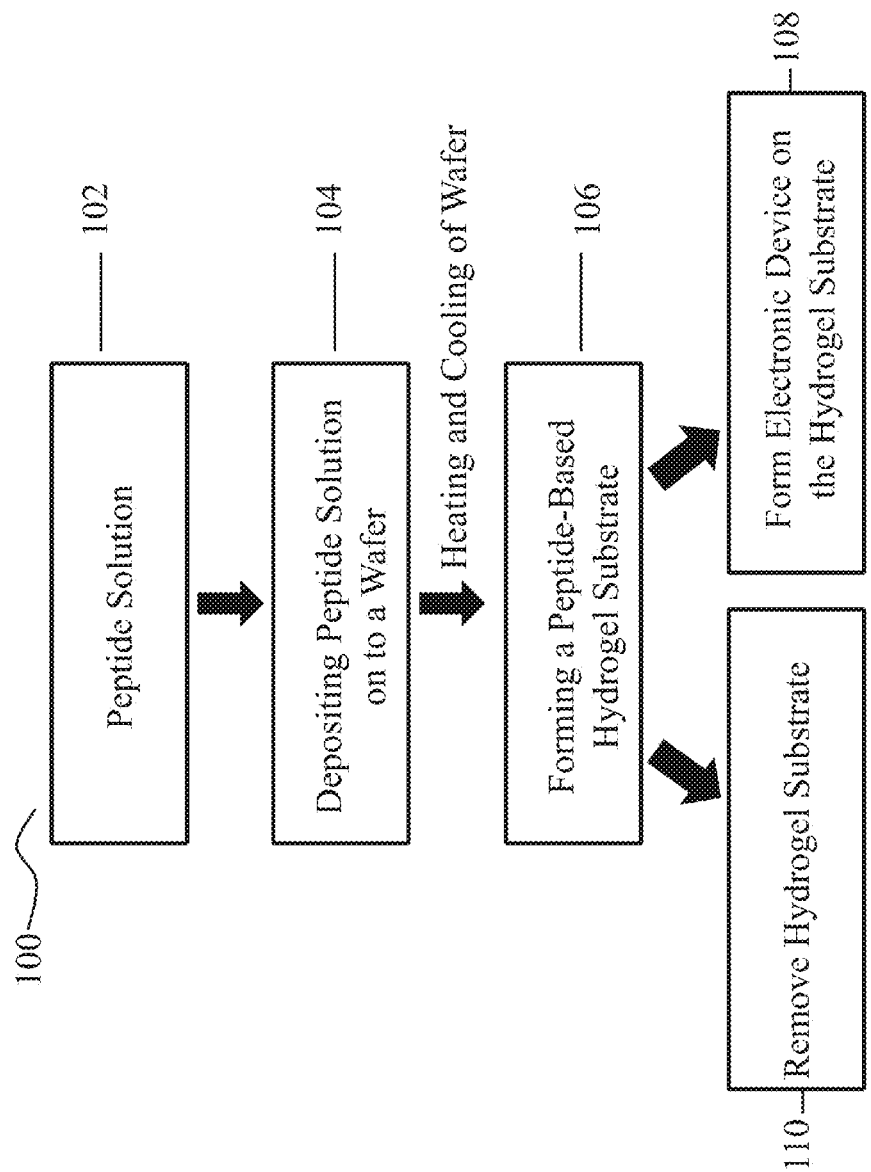
FIG. 1 is a flowchart illustrating exemplary steps for forming biocompatible structures of the present disclosure.

The present disclosure, which provides a method of forming a biocompatible structure that includes forming a biodissolvable substrate comprising a flexible network of peptides, and a biocompatible structure including a biodissolvable substrate having an electronic device on a surface thereof, will now be described in greater detail by referring to the following discussion and drawings that accompany the present disclosure. It is noted that the drawings are provided for illustrative purposes only and are not drawn to scale. It is also noted that like and corresponding elements are referred to by like reference numerals.

In the following description, numerous specific details are set forth, such as particular structures, components, materials, dimensions, processing steps and techniques, in order to provide an understanding of the various embodiments of the present application. However, it will be appreciated by one of ordinary skill in the art that the various embodiments of the present application may be practiced without these specific details. In other instances, well-known structures or processing steps have not been described in detail in order to avoid obscuring the present application.

It will be understood that when an element as a material, layer, region, wafer or substrate is referred to as being "on" or "over" another element, it can be directly on the other element or intervening elements may also be present. In contrast, when an element is referred to as being "directly on", "in direct contact with" or "directly over" another element, there are no intervening elements present. It will also be understood that when an element is referred to as being "beneath" or "under" another element, it can be directly beneath or under the other element, or intervening elements may be present. In contrast, when an element is referred to as being "directly beneath" or "directly under" another element, there are no intervening elements present. For purposes of the description hereinafter, the terms "upper", "lower", "vertical", "horizontal", "top", "bottom", and derivatives thereof shall relate to the structures disclosed herein, as they are oriented in the drawing figures.

The method of the present disclosure includes forming a solution of peptides and depositing a layer of the peptide-based solution on a surface of a wafer. The layer of peptide-based solution is then heated and subsequently cooled to form a flexible, peptide-based hydrogel on the wafer (i.e., biodissolvable substrate). The term "biodissolvable" as used herein refers to a material that is susceptible to being broken-down by naturally occurring reagents present in a biological environment. For example, a peptide may be broken down by an enzyme that reacts with the peptide at issue. In another example, a peptide (i.e., biodissolvable peptide) can be digested by a naturally occurring peptidase, such as tripsin. In one embodiment, an acid present in the human body can dissolve the bonds between certain amino acids of a polypeptide. In an in vivo application, the chemical moieties resulting from such a chemical break down can be cleared or further processed by the subject or neighboring tissue. A biodissolvable material that is "completely" dissolved is no longer detectable using standard tests known by one of ordinary skill in the art.

The substrate can then be separated from the wafer and implanted in a subject, such as an animal, preferably a human. Optionally, electronic devices that include at least one semiconductor component, such as a gate structure and/or interconnect, can be formed on an exposed surface of the biodissolvable substrate and then removed from the wafer and implanted on the surface of or within a subject. The flexible, peptide-based substrate is unique in comparison to other biocompatible substrates, such as silk substrates, in that the peptide-based substrate of the present disclosure is easily broken down (i.e., dissolved) by naturally-occurring enzymes present in the subject. Additionally, the peptides used to form the flexible, biodissolvable substrate of the present disclosure are tunable, which facilitates their use in a wide variety of applications. This method will now be described in greater detail by referring to FIGS. 1-4.

Referring first to FIG. 1, there is illustrated a flowchart for an exemplary method of forming a biocompatible structure 100 of the present disclosure. Step 102 in FIG. 1 illustrates the formation of a peptide-based solution 20 as further depicted in FIG. 2. As used herein the phrases "peptide-based solution" and "peptide solution" will be used interchangeably to describe a solution containing a predetermined concentration of peptide in a solvent. In one embodiment, the at least one subset of peptide is dissolved at a concentration from 0.1 µg/ml to 100 mg/ml to form a peptide-based solution of the present disclosure. In another embodiment, the peptide solution includes at least a first subset of peptide and a second subset of peptide, wherein the first and second subsets of peptide vary in amino acid length and/or composition. In another embodiment, the at least one subset of peptide is dissolved in solvent at a concentration of at least 0.1 mg/ml. In certain embodiments, the at least one peptide is dissolved at a concentration of 1.0 mg/ml to 50 mg/ml. In other embodiments, the at least one peptide is dissolved at a concentration of 0.1 mg/ml to 10 mg/ml, 1 mg/ml to 10 mg/ml or 1 mg/ml to 5 mg/ml. In a specific embodiment, the at least one peptide is dissolved in distilled water a concentration from 0.1 mg/ml to 10 mg/ml. However, specific concentrations of peptide in solution are also desirable to achieve certain physical characteristics such as mechanical or tensile strength of the resulting biodissolvable hydrogel substrate. For example, in some embodiments, the at least one peptide is dissolved at a concentration of 1 mg/ml, 1.5 mg/ml, 2 mg/ml, 2.5 mg/ml, 3 mg/ml, 3.5 mg/ml, 4 mg/ml, 4.5 mg/ml, 5 mg/ml, 5.5 mg/ml, 6 mg/ml, 6.5 mg/ml, 7 mg/ml, 7.5 mg/ml, 8 mg/ml, 8.5 mg/ml, 9 mg/ml, 9.5 mg/ml or 10 mg/ml.

Any peptide can be used to form a peptide-based solution of the present disclosure. For example, peptides can be naturally occurring, isolated and purified using known methods or synthesized to be substantially pure (i.e., having a purity of 95% or greater). Generally, peptides for use in the present methods are stable in an aqueous solution at physiological conditions at room temperature (i.e., 20° C. to 21° C.) for a period of time in the range from 1 day to at least 6 months, or to at least 8 months. In a specific embodiment, the range is from 1 day to at least 12 months. In one embodiment, the peptide is stable in aqueous solution at physiological conditions, at a temperature up to 90° C., for at least 1 hour.

Exemplary peptides for use in the present disclosure have a length of 2 to 20 amino acids and are capable of self-assembly into fibers (i.e., peptide amphiphiles), which form a flexible fibrous network of proteins (302) as described in further detail below. In a specific embodiment, amphiphilic peptides capable of self-assembling into three-dimensional macromolecular nanofibrous networks are mixed in solution, which entrap water to form a hydrogel. Generally, the term "peptide amphiphile(s)" or "amphiphilic peptide" used herein means a peptide composed of at least two linked amino acids that self-assemble into protein nanofibers in solution. Peptide amphiphiles can include multiple domains, such as a hydrophilic portion and hydrophobic portion, whereby self-assembly occurs when individual peptides bond (e.g., hydrogen- and π-bonding) to adjacent peptides in solution.

The mechanical and biological properties of the resulting peptide-based network are highly dependent on the amino acid sequence of individual peptides or mixture of peptides in solution. In certain embodiments, the peptides of the present disclosure are amphiphilic peptides comprising at least 2 or at least 3 amino acids. In other embodiments, the amphiphilic peptides added to a peptide solution 20 have a length of 2 to 10 amino acids, 2 to 8 amino acids, 2 to 6 amino acids or 2 to 4 amino acids, preferably 2, 3, 4, 5, 6, 7, 8, 9 or 10 amino acids. In a specific embodiment, the peptides of the present disclosure have a length of 2 to 3 amino acids. In one embodiment, the amphiphilic peptides added to the peptide-based solution 20 are tyrosine (Y)-leucine (L), tyrosine (Y)-alanine (A), tyrosine (Y)-serine (S), phenylalanine (F)-phenylalanine (F) and phenylalanine (F)-phenylalanine (F)-phenylalanine (F).

In a specific embodiment of the present disclosure, the peptide solution 20 is formed by mixing 9-fluorenyl-methoxycarbonyl (Fmoc) or pyrene (Pyr) and a plurality of peptide amphiphiles in an aqueous solution. In another embodiment, the peptide-based solution 20 includes Fmoc or Pyr and a plurality of 2 to 3 amino acid peptide amphiphiles. In other embodiments, the peptide-based solution 20 includes Fmoc or Pyr and only 2 amino acid amphiphiles. In an alternative embodiment, the peptide-based solution 20 includes Fmoc or Pyr and only 3 amino acid peptide amphiphiles. In another embodiment, the peptide-based solution 20 includes Fmoc or Pyr and a combination of 2 amino acid and 3 amino acid protein amphiphiles dissolved in aqueous solution. More specifically, the peptides of the peptide-based solution 20 are Fmoc-Y-L, Fmoc-Y-A, Fmoc-Y-S, Fmoc-F-F, Fmoc-F-F-F, Pyr-Y-L, Pyr-Y-A, Pyr-Y-S, Pyr-F-F, and Pyr-F-F-F.

Generally, solvents for use in the present methods are aqueous solutions, for instance in physiologically compatible buffers such as Hanks's solution, Ringer's solution, or a physiological saline buffer. In certain embodiments, peptides are dissolved in suitable organic solvents or solvent mixtures. In other embodiments, the peptides are dissolved in a chloroform, dimethyl sulfoxide (DMSO), dimethylformamide (DMF), acetic acid, acetonitrile, methanol, propanol, or isopropanol. In specific embodiments, the peptides are dissolved in water, such as double-distilled water at a desired concentration.

In other embodiments, the peptide-based solution 20 also includes additional components. In specific embodiments, the aqueous solution comprises peptides, water and a predetermined concentration of salt. More specifically, the peptides are dissolved in phosphate-buffered saline (PBS). In embodiments of the present method, whereby the peptide-based solution comprises a salt (NaCl), the mechanical strength of the resulting hydrogel increases as salt concentration increases. For example, in the presence of higher salt concentration such as saline and phosphate-buffered saline the hydrogels will have a significantly higher tensile strength when compared to hydrogels formed using peptides solvated in pure water.

In some embodiments, the peptide-based solution 20 can also include polymers, or additives such as at least one of a microorganism, a cell, collagen, gelatin, a nucleic acid, an oligosaccharide, a polysaccharide, a vitamin, an inorganic molecule, a microparticle, a synthetic polymer, a small organic molecule, a cosmetic agent or a pharmaceutically active compound.

Figure 2:
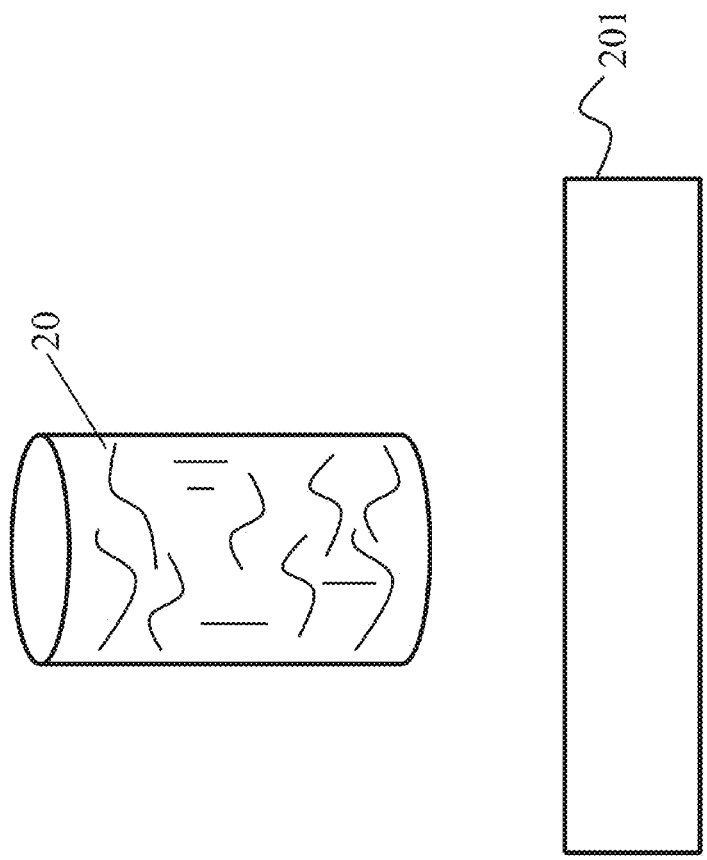
FIG. 2 is a cross sectional view of an exemplary wafer of the present disclosure and the mixing of a protein-based solution of the present disclosure.

The peptide solution 20 shown in FIG. 2 is formed by combining a plurality of peptides and a volume of an aqueous solution in a receptacle and mixing at a predetermined temperature over time. Generally, mixing occurs at a temperature and over a duration that facilitates self-assembly of peptide fiber-based networks. For example, a predetermined amount of a plurality of peptides can be added to solution (e.g., water or phosphate buffered saline) and continuously mixed on a rocker or with a magnetic stirring for 1 to 60 minutes, several hours, a day, several days or even a week at room temperature. However, in some embodiments the temperature at which the peptide solution is mixed can vary from approximately 20° C. to 30° C. or higher.

Referring to FIG. 2, a wafer 201 is provided, on which the peptide-based solution 20 is deposited as illustrated in step 104 of the exemplary method 100 shown in FIG. 1. The wafer 201 may comprise a semiconducting material, an insulating material, a conductive material or any combination thereof. When the wafer is comprised of a semiconducting material, any material having semiconductor properties or alloys thereof, may be used. The term "semiconductor" as used herein generally refers to any material that is an insulator at a very low temperature, but which has an appreciable electrical conductivity at elevated temperatures (i.e., a temperature of above 300 Kelvin). In the present disclosure, the term semiconductor is intended to be consistent with use of this term in the art of and electronic devices. A semiconductor material for use in the instant methods and structures include elemental semiconductors, such as silicon, germanium and diamond, and compound semiconductors, such as group IV compound semiconductors such as SiC and SiGe, group III-V semiconductors such as AlSb, AlAs, AlN, AlP, BN, BP, BAs, GaSb, GaAs, GaN, GaP, InSb, InAs, InN, and InP, group III-V ternary semiconductors alloys such as $Al_xGa_{1-x}As$, group II-VI semiconductors such as CsSe, CdS, CdTe, ZnO, ZnSe, ZnS, and ZnTe, group I-VII semiconductors such as CuCl, group IV-VI semiconductors such as PbS, PbTe, and SnS, layer semiconductors such as $PbI_2$, $MoS_2$, and GaSe, oxide semiconductors such as CuO and $Cu_2O$. The term semiconductor includes intrinsic semiconductor materials and extrinsic semiconductors that are doped with one or more selected materials, including semiconductors having p-type doping materials and n-type doping materials, to provide beneficial electronic properties useful for a given application or device. The term semiconductor includes composite materials comprising a mixture of semiconductors and/or dopants. Specific semiconductor materials useful for some embodiments include, but are not limited to, Si, Ge, Se, diamond, fullerenes, SiC, SiGe, SiO, $SiO_2$, SiN, AlSb, AlAs, AlIn, AlN, AlP, AlS, BN, BP, BAs, $As_2S_3$, GaSb, GaAs, GaN, GaP, GaSe, InSb, InAs, InN, InP, CsSe, CdS, CdSe, CdTe, $Cd_3P_2$, $Cd_3As_2$, $Cd_3Sb_2$, ZnO, ZnSe, ZnS, ZnTe, $Zn_3P_2$, $Zn_3As_2$, $Zn_3Sb_2$, $ZnSiP_2$, CuCl, PbS, PbSe, PbTe, FeO, $FeS_2$, NiO, EuO, EuS, PtSi, TlBr, $CrBr_3$, SnS, SnTe, $PbI_2$, $MoS_2$, GaSe, CuO, $Cu_2O$, HgS, HgSe, HgTe, $HgI_2$, MgS, MgSe, MgTe, CaS, CaSe, SrS, SrTe, BaS, BaSe, BaTe, $SnO_2$, TiO, $TiO_2$, $Bi_2S_3$, $Bi_2O_3$, $Bi_2Te_3$, $BiI_3$, $UO_2$, $UO_3$, $AgGaS_2$, $PbMnTe$, $BaTiO_3$, $SrTiO_3$, $LiNbO_3$, $La_2CuO_4$, $La_{0.7}Ca_{0.3}MnO_3$, CdZnTe, CdMnTe, $CuInSe_2$, copper indium gallium selenide (CIGS), HgCdTe, HgZnTe, HgZnSe, PbSnTe, $Tl_2SnTes$, $Tl_2GeTes$, AlGaAs, AlGaN, AlGaP, AlInAs, AlInSb, AlInP, AlInAsP, AlGaAsN, GaAsP, GaAsN, GaMnAs, GaAsSbN, GaInAs, GaInP, AlGaAsSb, AlGaAsP, AlGaInP, GaInAsP, InGaAs, InGaP, InGaN, InAsSb, InGaSb, InMnAs, InGaAsP, InGaAsN, InAlAsN, GaInNAsSb, GaInAsSbP, and any combination of these. Porous silicon semiconductor materials are useful for aspects described herein. Impurities of semiconductor materials are atoms, elements, ions and/or molecules other than the semiconductor material(s) themselves or any dopants provided to the semiconductor material. Impurities are undesirable materials present in semiconductor materials which may negatively impact the electronic properties of semiconductor materials, and include but are not limited to oxygen, carbon, and metals including heavy metals. Heavy metal impurities include, but are not limited to, the group of elements between copper and lead on the periodic table, calcium, sodium, and all ions, compounds and/or complexes thereof. In addition to these listed types of semiconducting materials, the wafer 201 can be comprised of glass, metal or a polymer.

When the wafer 201 is an insulating material, the insulating material can be an organic insulator, an inorganic insulator or a combination thereof including multilayers. Some examples of insulating or dielectric materials can be non-porous or porous materials. Other suitable dielectrics that can be used as dielectric wafer material include, but are not limited to, $SiO_2$, silsesquioxanes, C-doped oxides (i.e., organosilicates) that include atoms of Si, C, O and H, thermosetting polyarylene ethers, or multilayers thereof. The term "polyarylene" is used in this application to denote aryl moieties or inertly substituted aryl moieties which are linked together by bonds, fused rings, or inert linking groups such as, for example, oxygen, sulfur, sulfone, sulfoxide, carbonyl and the like. The insulating wafer material generally has a dielectric constant that is about 4.0 or less, with a dielectric constant of about 2.8 or less being more typical. All dielectric constants mentioned herein are relative to a vacuum, unless otherwise noted.

The thickness of such a wafer 201 may vary depending upon the type of material used as well as the exact amount and composition of peptide solution being deposited thereon. Typically, wafer 201 has a thickness from 50 nm to 500 microns. In certain embodiments the wafer has a thickness of between 100 nm and 100 microns, or between 100 nm and 1 micron.

When the wafer 201 is a conducting material, the wafer 201 may include, for example, polySi, an elemental metal, alloys of elemental metals, a metal silicide, a metal nitride or any combination thereof including multilayers.

Figure 3:
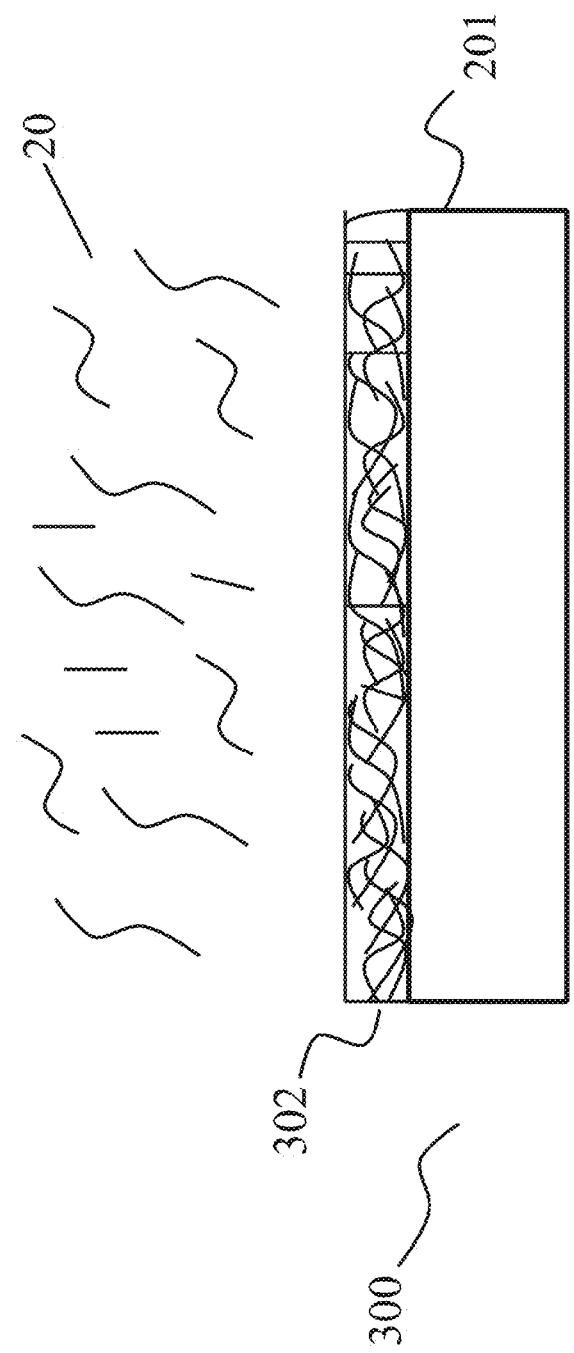
FIG. 3 is a cross sectional view of an exemplary biocompatible structure having a biodissolvable substrate on a top surface of the wafer shown in FIG. 2.

As depicted in FIG. 3 and step 104 of the exemplary embodiment set forth in FIG. 1, the peptide solution 20 is deposited on an exposed surface of the wafer 201 forming a layer of peptide-based solution 302 on the wafer 201. Numerous methods can be used to apply the solution 20 to the wafer 201. These methods include dip coating, spray coating, brush coating, roll coating, or spin casting a film layer onto the wafer, typically followed by mild heating to promote adhesion to the surface. Solid free form processes such as three dimensional printing techniques (3DP), or freeze drying methods could be used to create complex three-dimensional structures, including porous structures. The term "substrate" as used herein refers to a material, layer or other structure having a surface, such as a receiving surface, that is capable of supporting one or more components or electronic devices. A component can be affixed to a substrate such that the component is in physical contact with the substrate and unable to substantially move relative to the substrate surface to which it is affixed.

In a specific embodiment of the present disclosure, the peptide based solution is spin coated onto a surface of the wafer 201 at spin rates from 500 rpm to 3000 rpm for a predetermined period of time, suitable to permit the application of a contiguous layer of peptide based solution 302 on the wafer, whereby the peptide solution layer 302 has a thickness of between 50 nm and 100 microns. For example, in certain embodiments, the peptide based solution is spin coated onto a surface of the wafer 201 for between 30 seconds and 120 seconds, inclusive. In other embodiments, the peptide based solution is spin coated onto a surface of the wafer 201 for about 30 seconds, about 45 seconds, about 60 seconds, about 75 seconds, about 90 seconds, about 105 seconds, or about 120 seconds. The phrase "contiguous" refers to materials or layers that are touching or connected throughout in an unbroken sequence. In one embodiment, a contiguous layer of peptide amphiphile solution 302 is formed across an entire topmost surface of a wafer 201, as shown in FIG. 3. The duration of spin coating can be determined by the desired thickness of the resulting layer of peptide solution 302. That is, shorter durations of application will result in a thinner layer of peptide solution 302 on the surface of wafer 201, while a longer application of peptide solution 20 on the surface of wafer 201 will result in a thicker, more rigid layer of peptide solution 302. In specific embodiments, the peptide-based solution 20 is spin cast onto the wafer 20 at spin rates between 1000 and 4000 rpm, 1000 and 3000 rpm, or 1000-2000 rpm for at least thirty (30) seconds. In other embodiments the peptide solution 20 is spin cast onto the wafer 20 at spin rates between 2000 and 3000 rpm for 30 seconds. In an exemplary embodiment, the peptide solution 20 is spin cast onto the wafer 20 at spin rates between 2000 and 3000 rpm for 60 seconds.

In embodiments where a flexible, biodissolvable hydrogel substrate 302a is formed from the peptide-based solution 20, processing step 106 is carried out for a predetermined period of time. Step 106 in FIG. 1 includes a first heating step, for example, heating the applied solution 20 under vacuum, in air, water, water vapor, supercritical $CO_2$ or another environment that favors the peptide component of the solution.

Such a first heating step includes heating the solution to at least 30° C. but below the melting point of the peptide for at least one minute. In other embodiments, the peptide-based solution 20 is heated to a temperature of between 30° C. and 80° C.

In certain embodiments, the heating step of process step 106 can be repeated at least once or more. In some embodiments, multiple heating steps can be carried out at the same or different temperatures. For example, process step 106 can include a first heating step comprising heating the solution to 30° C. for at least one minute, and a second heating step comprising heating the solution for an additional period of time to a temperature greater than 30° C.

Subsequently, the resulting solution is cooled over time at a temperature of about 20° C. Such a cooling step occurs for a duration of at least one minute or until the contiguous layer of peptide solution 302 forms a hydrogel, i.e., a flexible biodissolvable hydrogel 302a as shown in FIG. 4. In other embodiments the resulting solution is cooled for a duration of at least 10 minutes, at least 15 minutes, at least 20 minutes, at least 25 minutes, at least 30 minutes, at least 35 minutes or greater to form a hydrogel. In specific embodiments, the solution in step 106 is cooled at a temperature of between 20° C. and 21° C. for about 30 minutes.

In certain embodiments, the heating and cooling steps of process step 106 can be repeated at least once or more. In some embodiments, multiple heating and cooling steps can be carried out at the same or different temperatures. For example, process step 106 can include a first heating step comprising heating the solution at 30° C. for at least one minute, and a first cooling step comprising cooling the resulting solution to 20° C. Next, the solution layer 302 can be subjected to a second heating step comprising heating the solution for an additional period of time (e.g., at least 1 minute) at a temperature greater than 30° C., and subsequently cooling the solution layer 302 at a temperature of between 20° C. and 21° C. for about 30 minutes to form a flexible hydrogel 302a on the surface of wafer 201.

The physical and mechanical properties of the flexible hydrogel substrate 302a of the present disclosure can be tuned as desired based on the peptide concentration and characteristics. For example, the thickness and mechanical strength of the biodissolvable hydrogel substrate 302a can vary based on peptide concentration and thickness of the hydrogel. One example of a tunable mechanical property of the hydrogel substrate 302(a) of the present disclosure is Young's modulus. The term "Young's modulus" is a mechanical property of a material, device or layer such as the biodissolvable substrate 302a of the present disclosure, which refers to the ratio of stress to strain for a given substance. Young's modulus may be provided by the expression:

$$E = (\text{stress})(\text{strain}) = (L0\Delta L)FA), \qquad (\text{I})$$

where E is Young's modulus, $L_0$ is the equilibrium length, $\Delta L$ is the length change under the applied stress, F is the force applied, and A is the area over which the force is applied. Young's modulus may also be expressed in terms of Lame constants via the equation:

$$E = \mu(3\lambda + 2\mu)\lambda + \mu, \qquad (\text{II})$$

where $\lambda$ and $\mu$ are Lame constants. High Young's modulus (or "high modulus") and low Young's modulus (or "low modulus") are relative descriptors of the magnitude of Young's modulus in a given material, layer or device. In some embodiments, a high Young's modulus is larger than a low Young's modulus, preferably about 10 times larger for some applications, more preferably about 100 times larger for other applications, and even more preferably about 1000 times larger for yet other applications. In an embodiment, a low modulus layer has a Young's modulus less than 100 MPa, optionally less than 10 MPa, and optionally a Young's modulus selected from the range of 0.1 MPa to 50 MPa. In an embodiment, a high modulus layer has a Young's modulus greater than 100 MPa, optionally greater than 10 GPa, and optionally a Young's modulus selected from the range of 1 GPa to 100 GPa.

As shown in step 110, the biodissolvable hydrogel substrate 320a can be removed (e.g., separated) from the underlying wafer 201 to provide a first exemplary biocompatible structure of the present disclosure, which includes a flexible biodissolvable network of peptides. The phrase "biocompatible" refers to a material that does not elicit an immunological effect or reaction when it is disposed within a subject or biological environment.

For example, the biodissolvable hydrogel substrate 320a may be mechanically removed from the surface of the wafer 201 by, for example, peeling to break the interfacial stresses (bonds) between layers. The resulting biodissolvable substrate can then be implanted within or on a subject on the soft, curvilinear surfaces of bone or other biological tissues (e.g., skin, or organ tissue).

Step 108 in the exemplary method depicted in FIG. 1 shows an alternative embodiment whereby, prior to removal of the biodissolvable hydrogel substrate 320a, an electronic device 404 comprising at least one semiconductor component is formed on an exposed surface of the substrate. The term "electronic device" means a device incorporating a plurality of components, printed wire boards, integrated circuits, transistors, gate structures, arrays, biological, chemical and/or physical sensors. The biocompatible devices of the present disclosure allow for the use of electronic devices in a variety of in vivo biomedical applications without having to retrieve the devices and/or their components because they are completely biodissolvable and/or not harmful to the in vivo environment of the subject in which they are implanted.

As shown in FIG. 4, an electronic device 404 is formed on a topmost surface of the underlying biodissolvable substrate 320a, which provides a second biocompatible structure 400 of the present disclosure. The term "component" is used broadly to refer to an individual element of a compilation of elements. A "gate electrode" or "gate conductor" is one example of a device component, and refers to an electrically conducting structure capable of establishing an electrical connection with another component. Another non-limiting example of a component is a wafer or a dielectric layer. Components may be connected to one or more elements as known in the art, such as by metal evaporation, wire bonding, and application of solids or conductive pastes. A "semiconductor component" refers to any semiconductor material or structure, and including, for example, single crystalline and polycrystalline semiconductors, doped semiconductor materials, inorganic semiconductors, and composite semiconductor materials.

FIG. 4 depicts the formation of an electronic device 404 on a topmost surface of the biodissolvable substrate 320a, whereby the electronic device is a gate structure. Additional exemplary biocompatible electronic devices include biodegradable Schottky diodes, biodegradable capacitors, and biodegradable optical devices.

FIG. 4 depicts one embodiment of forming a gate structure 404 on biodissolvable substrate 320a. The gate structure 404 that is depicted in FIG. 4 can be formed utilizing deposition, photolithography and etch process steps. For example, a component or material layer 401, 402, 403 of the gate structure 404 may be deposited over the biodissolvable substrate 320a. Thereafter, a pattern corresponding to the geometry of a gate structure can be formed overlying the deposited component or material layer by, for example, applying a photoresist to the surface to be etched, exposing the photoresist to a pattern of radiation, and then developing the pattern into the photoresist utilizing a resist developer. Once the patterning of the photoresist is completed, the sections covered by the patterned photoresist are protected while the exposed regions are removed using a selective etching process that removes the unprotected regions.

In one embodiment, the gate structure 404 includes at least one gate dielectric 401 that is present on, e.g., in direct contact with, the biodissolvable substrate 320a, and at least one gate conductor 402 that is present on the at least one gate dielectric 401. The gate structure 404 may also include a gate dielectric cap 403 that is present on an upper surface of the at least one gate conductor 402.

In some embodiments, at least one spacer (not shown) may be formed in direct contact with the gate structure 404. The spacer may be composed of a dielectric material, such as an oxide, nitride or oxynitride material. Spacers may be formed using deposition and etch processes known in the art.

Materials for use in fabricating the electronic devices of the present disclosure include biocompatible materials, such as those previously approved by the Food and Drug Administration (FDA). Generally, the term "biocompatible materials" as used herein refers to materials that not harmful to the environment, whereby the environment is the endogenous, in vivo environment of the body of a subject. Specific examples, of such biocompatible materials include, but are not limited to, Zinc (Zn), Magnesium (Mg), Silicon (Si), Gallium nitride (GaN) and alloys thereof.

The biocompatible structures of the present provide base technology for implantable integrated electronic systems for, e.g., biosensing or drug-delivery applications. These systems may also be implanted or affixed to a subject for temporary monitoring of a biological or physical property. Additionally, a biocompatible structure of the present disclosure can be used as a drug-delivery device equipped with biodegradable integrated circuit technology. Moreover, networks of biodegradable electronic devices may also be used for temporarily monitoring biological or physical activity of a subject.

While the present disclosure has been particularly shown and described with respect to preferred embodiments thereof, it will be understood by those skilled in the art that the foregoing and other changes in forms and details may be made without departing from the spirit and scope of the biocompatible structures and methods of forming the same provided herein. It is therefore intended that the present disclosure not be limited to the exact forms and details described and illustrated, but fall within the scope of the appended claims.

What is claimed is:

1. A method of forming a biocompatible structure, said method comprising:
   forming a solution comprising a plurality of peptides;
   depositing said solution on a surface of a wafer, and
   forming a biodissolvable substrate on said surface of said wafer.

2. The method of claim 1, further comprising forming an electronic device on an exposed surface of said biodissolvable substrate.

3. The method of claim 2, wherein said electronic device comprises at least one semiconductor component.

4. The method of claim 1, wherein forming said solution comprises mixing 9-fluorenylmethoxycarbonyl (Fmoc) or pyrene (Pyr) and a plurality of peptide amphiphiles in water.

5. The method of claim 4, wherein said solution comprises 0.1 mg/ml of peptide to 10 mg/ml of peptide.

6. The method of claim 4, wherein a first subset of said plurality of peptide amphiphiles are two amino acids in length.

7. The method of claim 6, wherein a second subset of said plurality of peptide amphiphiles are at least 3 amino acids in length.

8. The method of claim 4, wherein said peptide amphiphiles of said plurality of peptide amphiphiles are either two amino acids in length or three amino acids in length.

9. The method of claim 1, wherein said deposition comprises spin coating said solution on an exposed surface of said wafer at a spin rate between 500 rpm and 3000 rpm.

10. The method of claim 9, wherein said forming said biodissolvable substrate comprises heating said solution to a temperature of at least 30° C. and subsequently cooling said solution to a temperature of about 20° C.

11. A biocompatible structure comprising:
a biodissolvable substrate, wherein said biodissolvable substrate comprises a flexible network of peptides; and
an electronic device having at least one semiconductor component on said substrate.

12. The structure of claim 11, wherein said flexible network of peptides comprises a mixture of 9-fluorenylmethoxycarbonyl (Fmoc) or pyrene (Pyr) and a plurality of peptide amphiphiles.

13. The structure of claim 11, wherein said biodissolvable substrate has a thickness from 100 nanometers to 500 microns.

14. The structure of claim 11, wherein at least one of said semiconductor components is a flexible semiconductor component or a stretchable semiconductor component.

15. The structure of claim 11, wherein a bottommost surface of said electronic device is in direct physical contact with a topmost surface of said biodissolvable substrate.

16. A biocompatible structure comprising:
a biodissolvable substrate, wherein said biocompatible substrate has a Young's modulus selected from the range of 0.5 MPa and 10 GPa; and
an electronic device having at least one semiconductor component on said substrate.

17. The structure of claim 16, wherein at least one of said semiconductor components is a flexible semiconductor component or a stretchable semiconductor component.

18. The structure of claim 16, wherein a bottommost surface of said electronic device is in direct physical contact with a topmost surface of said biodissolvable substrate.

* * * * *